United States Patent
Everett et al.

(10) Patent No.: US 6,431,751 B1
(45) Date of Patent: Aug. 13, 2002

(54) CEILING MOUNTED, TRANSPORTABLE, SURGICAL C-ARM WITH FLAT PANEL IMAGE RECEPTOR

(75) Inventors: Dennis K. Everett, Seven Hills; Leonard F. Plut, Concord; Donald E. Negrelli, Gates Mills; John A. Shovary, Solon; William C. Widlicka, Chardon, all of OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/664,506

(22) Filed: Sep. 18, 2000

(51) Int. Cl.[7] .................................................. H05G 1/02
(52) U.S. Cl. ........................................ 378/197; 378/193
(58) Field of Search ................................ 378/193, 197, 378/198

(56) References Cited

U.S. PATENT DOCUMENTS

| | | | |
|---|---|---|---|
| 2,818,510 A | 12/1957 | Verse | |
| 4,150,297 A | 4/1979 | Brggren | 250/490 |
| 5,226,069 A * | 7/1993 | Narita | 378/197 |
| 5,327,474 A | 7/1994 | Inoue et al. | 378/20 |
| 5,521,957 A * | 5/1996 | Hansen | 378/198 |
| 5,901,200 A * | 5/1999 | Krause | 378/198 |
| 6,031,888 A | 2/2000 | Ivan et al. | 378/20 |
| 6,222,906 B1 * | 4/2001 | Sakaguchi et al. | 378/98.8 |
| 6,285,902 B1 * | 9/2001 | Kienzle, III et al. | 600/427 |

OTHER PUBLICATIONS

Swissray Advertisement, *Medical Imaging*, vol. 12, No. 9, Sep., 1997.
Picker Internationa, Orbitor HF Mobile C–Arms Product Data Sheet, 1994.
FischerImaging Product Data Sheet—Ceiling Suspended Imaging System.

* cited by examiner

*Primary Examiner*—Robert H. Kim
*Assistant Examiner*—Jurie Yun
(74) *Attorney, Agent, or Firm*—Fay, Sharpe, Fagan, Minnich & McKee, LLP

(57) ABSTRACT

A diagnostic imaging system with a C-arm (12) for supporting an x-ray source (28) and a flat panel image receptor (30). The C-arm further including a coupler (36) that permits the C-arm (12) to be removably attached to different ceiling-mounted support structures (16), and to a mobile cart (92) for mobile C-arm imaging applications. A transport cart (62) is provided to transport the C-arm (12) from a first operating room to a second operating room. A mobile equipment cart (56) can accompany the transport cart (62). Alternately, a central control facility (72) can provide command and control signals for the C-arm.

20 Claims, 17 Drawing Sheets

CEILING MOUNTED, TRANSPORTABLE, SURGICAL C-ARM WITH FLAT PANEL IMAGE RECEPTOR

BACKGROUND OF THE INVENTION

The present invention relates to the diagnostic imaging arts. It finds particular application in conjunction with a ceiling mounted, transportable, surgical C-arm with a flat panel image receptor. However, it should be appreciated that the invention disclosed herein can find use in a variety of other applications.

Fixed, ceiling-supported C-arm imaging systems are high in cost, inefficient to use, and limited to use in only one room. Fixed systems cannot be used during the time that the room is being cleaned and prepared for a new patient. While mobile C-arm imagers avoid this problem and can be used in different rooms, due to the number of required components and necessary interconnecting cables, they result in crowded, cluttered operating rooms where floor space is at a premium. Also, conventional image amplifiers or intensifiers, due to their size, limit the surgeon's access to the patient.

Accordingly, it has been considered desirable to develop a new and improved ceiling-mounted, transportable, surgical C-arm that meets the above-stated needs and overcomes the foregoing difficulties and others while providing better and more advantageous results.

SUMMARY OF THE INVENTION

In accordance with one aspect of the present invention, a diagnostic imaging system is disclosed. The diagnostic imaging system includes a mounting structure adapted for attachment to a fixed surface, a support member with an x-ray source and an x-ray detector secured thereto, and a coupler that removably secures the support member to the mounting structure.

In accordance with another aspect of the present invention, a method of performing a diagnostic imaging procedure with a diagnostic imaging system is disclosed. The diagnostic imaging system includes a mounting structure secured to a fixed surface at a first location, a support member removably secured to the mounting structure by a coupler, and an x-ray source and an x-ray detector secured to the support member. The method includes a) disconnecting the support member from the mounting structure, b) transporting the support member from the first location to a second location, and c) operating the x-ray source and the x-ray detector to perform a diagnostic imaging procedure at the second location.

In accordance with yet another aspect of the present invention, a method of performing a diagnostic imaging procedure with a diagnostic imaging system is disclosed. The diagnostic imaging system includes a mounting structure, a support member secured to the mounting structure, and an x-ray source and an x-ray detector secured to the support member. The method includes a) disconnecting the mounting structure from a first fixed surface, b) transporting the mounting structure and support member from a first location to a second location, c) attaching the mounting structure to a second fixed surface at the second location, and d) operating the x-ray source and x-ray detector to perform a diagnostic imaging procedure at the second location.

One advantage of the present invention is the provision of a diagnostic imaging system that reduces operating room clutter and frees up floor space for various surgical procedures requiring x-ray imaging.

Another advantage of the present invention is the provision of a diagnostic imaging system that results in reduced capital expenditures, and reduced operating and maintenance expenses.

Still another advantage of the present invention is the provision of a diagnostic imaging system that permits an interventionalist to stand behind a flat panel image receptor which acts as a primary barrier to radiation exposure.

Yet another advantage of the present invention is the provision of a diagnostic imaging system that incorporates a flat panel image detector.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE INVENTION

Figure 1:
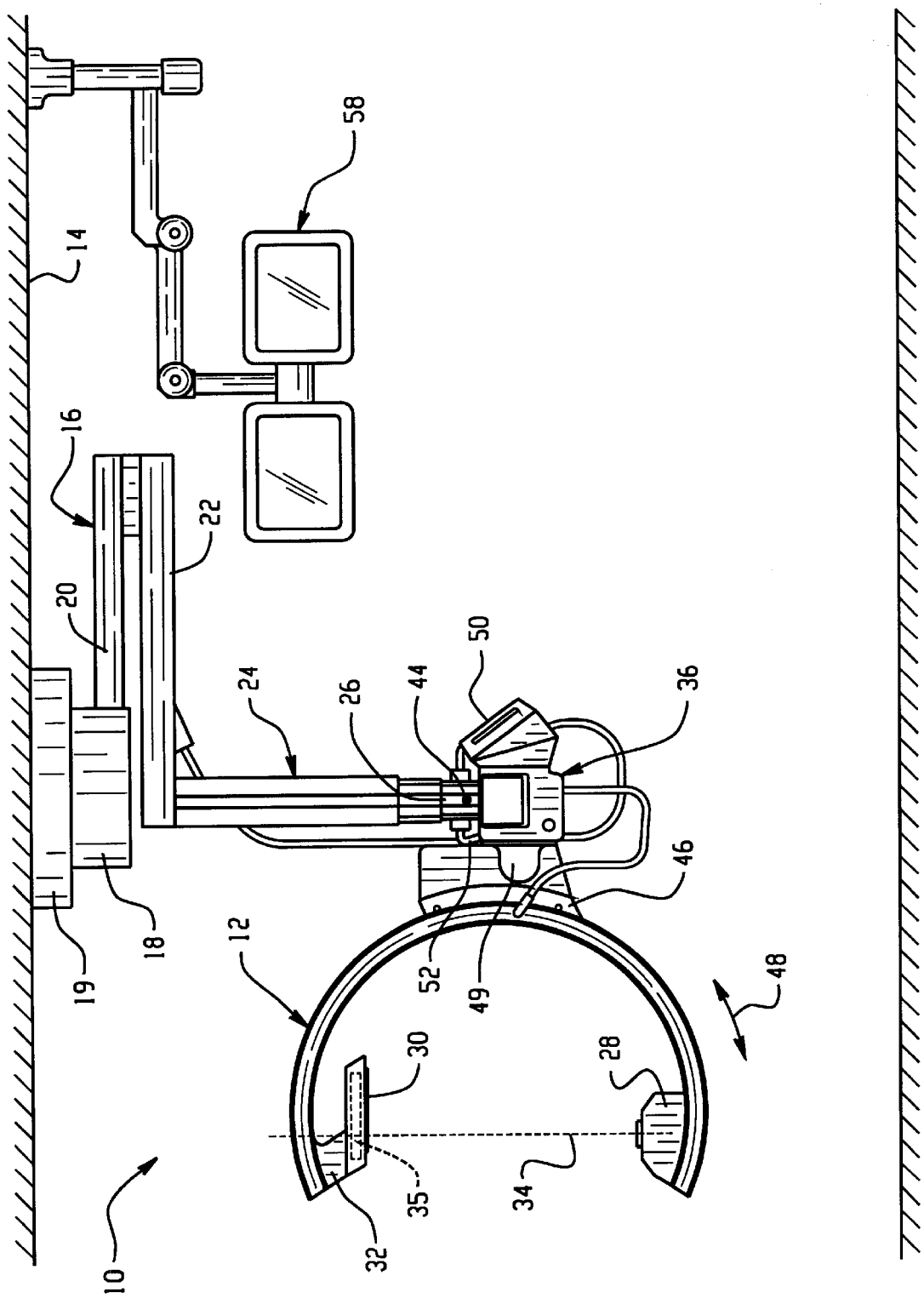
FIG. 1 illustrates a diagnostic imaging system with a transportable surgical C-arm suspended from a ceiling-mounted telescopic support arm, and with ceiling-mounted video monitors in accordance with one embodiment of the present invention.

With reference to FIG. 1, a diagnostic imaging system such as a fluoroscopic and/or radiographic imaging system 10 is shown. The imaging system 10 includes a transportable support member 12 that is suspended from a ceiling 14 by a mounting structure or telescopic support arm assembly 16.

In the embodiment being described, the mounting structure 16 includes a rotatable base member 18 secured to the ceiling 14 by a fixed ceiling mount 19. A first lateral boom or support arm 20 cantilevers from the base 18. A second lateral boom or support arm 22 is rotatably secured to, and cantilevers from, a free end of the first arm 20. An upright column assembly 24 includes a plurality of telescoping columns that cooperatively extend and retract from a free end of the second arm 22. As described in detail below, a lowermost column member 26 of the column assembly 24 is adapted to removably engage the support member 12 in an operational state of the diagnostic imaging system 10. It is contemplated that manual or solenoid-driven interlocks and/or position switches can be utilized to control or limit the movement of the various components of the mounting structure 16 including the base member 18, support arms 20, 22, and column members of the column assembly 24.

In the embodiment being described, the support member 12 is a C-arm. An x-ray source or tube 28 is secured to a first (e.g. lower) free end of the C-arm 12, and an opposing x-ray detector 30 is secured to a second (e.g. upper) free end of the C-arm 12. The x-ray source 28 and/or x-ray detector 30 can be mounted to the C-arm by a respective support bracket 32. A fluoroscopic/radiographic examination region is defined between the x-ray source and x-ray detector generally along a centerline 34. The x-ray source 28 and x-ray detector 30 can be positioned relative to the C-arm such that the centerline 34 is substantially coplanar with the C-arm along an axis projecting orthogonal to the drawing sheet of FIG. 1. Alternatively, as disclosed in U.S. Pat. No. 6,031,888, issued on Feb. 29, 2000, and assigned to the same assignee of the present invention, the centerline 34 can be offset (in directions orthogonal to the drawing sheet of FIG. 1) from the plane encompassing the C-arm by L-shaped support brackets in order to minimize the interference caused by the C-arm during interventional procedures.

The x-ray source 28 includes a housing that supports a fixed or rotating anode x-ray tube with an integral or separate high-voltage power supply. The x-ray detector 30 includes a housing which supports a flat panel image receptor 35. As is known in the art, the flat panel image receptor 35 generally includes a planar substrate such as glass laminated with an array of sensors such as amorphous silicon crystals that convert x-ray energy to electrical signals. That is, the sensors emit an electric potential when struck by photons of x-ray energy. The magnitude of the potential is related to the intensity of the x-ray beam. The electrical signals can be read out from a row/column matrix and then converted to digital data.

In one embodiment of the invention, the amorphous silicon flat panel image receptor 35 can include a Cesium Iodide scintillating layer on an amorphous silicon glass substrate. The scintillating layer converts x-ray energy into light. An array of photodiodes on the glass substrate convert the light into electrical signals. The electrical signals are read out of a row/column matrix that is accessed using thin film transistor switches on the amorphous silicon substrate. The analog data is then converted to a digital format for downstream processing. Suitable amorphous silicon-based, flat panel image receptors are described in U.S. Pat. Nos. 5,079,426; 5,117,114; 5,164,809; and 5,262,649.

It should be appreciated that the amorphous silicon flat panel image receptor 35 is compact in size and weight and replaces a conventional image intensifier tube, thus reducing the size of the x-ray detector 30. Further, the flat panel image receptor 35 provides a rectangular image, eliminates the distortion of an image common to conventional image intensifier tubes, and provides constant image quality across the flat panel of the image receptor, thus minimizing the amount of panning typically required with conventional image intensifier tubes. It should be appreciated that the flat panel image receptor 35 can be of any dimension such as 20 cm×25 cm, and the system can be easily upgraded to incorporate larger flat panel image receptors.

Figure 4:
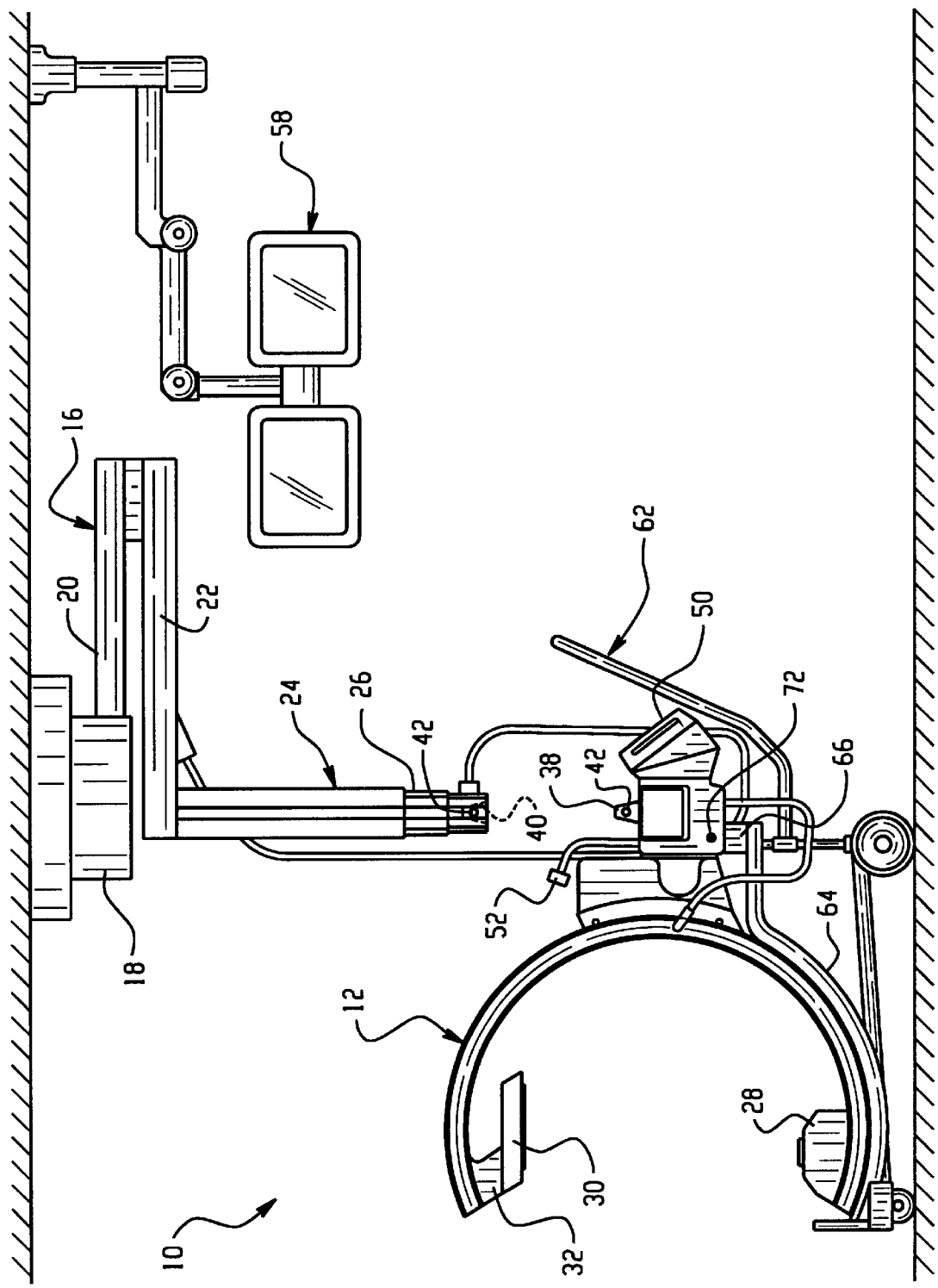
FIG. 4 illustrates the telescopic support arm in a retracted configuration once the C-arm has been secured to the transport cart of FIG. 2.

A coupler 36 associated with the C-arm 12 removably couples the C-arm to the lowermost column member 26 of the column assembly 24. As best shown in FIG. 4, the coupler 36 includes an upright, substantially conical or tapered mount or mounting pin 38 that projects from the coupler 36. The conical mount 38 is adapted to engage with a mutually conforming recess 40 associated with the lowermost column member 26. Transverse bores 42 extend through the conical mount 38 and the recess 40, and are adapted to mutually align and receive a locking pin 44 (FIG. 1) when the C-arm 12 is engaged with the mounting structure 16. The locking pin 44 can be manually inserted into (and removed from) the aligned bores 42. Alternatively, the locking pin 44 can be solenoid-driven under command from a system control panel discussed below.

Referring again to FIG. 1, the C-arm 12 is supported by a bearing assembly and associated interlock and position sensor 46 of the coupler 36. The bearing assembly 46 permits the C-arm 12 and depending x-ray source 28 and detector 30 to rotate or otherwise orbit in clockwise and counter-clockwise directions as shown by arrow 48 through an arc of at least 180° (±90°). Additionally, the bearing assembly 46 is supported by a rotary joint and associated interlock and position sensor 49 of the coupler 36. The rotary joint 49 permits the C-arm 12 and depending x-ray source 28 and detector 30 to rotate orthogonally into and out of the drawing sheet of FIG. 1 for generating cranial/caudal views of an imaged patient. Lastly, the C-arm 12 moves vertically as the column assembly 24 telescopically extends and retracts.

A control panel 50 of the coupler 36 controls the movement and/or positioning of the diagnostic imaging system 10 by controlling one or more of i) the rotation of the C-arm 12 about the bearing assembly 46, ii) the rotation of the C-arm about the rotary joint 49, iii) the extension and retraction of the column assembly 24, and iv) the rotation of the mounting structure 16 and depending C-arm about the ceiling 14. In particular, the control panel 50 is operatively connected to the various interlocks and drive mechanisms (e.g. motors) associated with the mounting structure components 18–26 and the coupler 36 through one or more quick-disconnect cables 52.

The x-ray source 28 and x-ray detector 30 of the diagnostic imaging system 10 are controlled (i.e. activated and deactivated) from a second control console and/or a data input device associated with the second control console, such as a foot pedal. For instance, as shown in FIGS. 6a–6d, the diagnostic imaging system 10 is controlled from one or more control consoles 54 associated with a transportable (i.e. wheeled) equipment cart 56. The equipment cart 56 includes known image reconstruction processing hardware and/or software for reconstructing an image representation from signals received from the x-ray detector 30. Preferably, the image reconstruction processor reconstructs a volumetric image representation from radiation attenuation data acquired by the x-ray detector 30.

Referring again to FIG. 1, one or more ceiling-mounted display monitors 58 convert selectable portions of the reconstructed volumetric image representation into a two-dimensional human-readable (i.e. viewable) display. The equipment cart 56 can also include tape and disk recording devices for archiving image representations, and also include circuitry for performing image enhancements, selecting planes, 3D renderings, or color enhancements, and the like. Various scanner control functions such as initiating a scan, selecting among different types of scans, calibrating the system, and the like, can also be performed at the control console 54 of the equipment cart 56. The equipment cart 56 can be operatively coupled to the diagnostic imaging system 10 (including the mounting structure 16, x-ray source 28, x-ray detector 30, display monitors 58 through data and/or power cables 60 (FIGS. 6a–6d). The power cables 60 can either be directly coupled to the various components of the diagnostic imaging system 10 or connected through one or more wall outlets 61.

When activated at the control console 54, the diagnostic imaging system, and, in particular, the x-ray source exposure 28, can be either continuous or pulsed. In the pulsed mode, radiography procedures can be performed, such as CINE, Spot Film and DSA, thereby generating radiographic image representations. The x-ray source 28 can be gated on and off in the pulsed mode using a conventional grid control circuitry or a pulse fluoro high-voltage power supply.

In order to achieve the stated objects of the present invention, the coupler 36 and depending C-arm 12 are removable from the mounting structure 16. In particular, a medical facility can achieve significant cost reductions in initial capital expenditures and in reduced maintenance and operating expenses by providing a single or limited number of support arms 12 that can be easily and rapidly transported between multiple operating rooms on an as-needed basis.

Prior to transporting the C-arm 12 from a first operating room to a second operating room, the C-arm 12 is driven into a "make ready for transport" position as shown in FIG. 1. That is, the C-arm 12 is manually or automatically driven to i) position the C-arm orbit at a null or zero degrees (controlled by bearing assembly 46), ii) position the Cranial/Caudal pivot at null or zero degrees (controlled by rotary joint 49), and iii) position the vertical drive at a predetermined limit (such as five inches from a low limit)(controlled by column assembly 24). It is contemplated that position sensors can be provided to verify or confirm that the C-arm has been properly placed into the "make ready for transport" position. If automatically driven, a single "activate docking position" switch, associated with the diagnostic imaging system (e.g. mounting structure 16, control panel 50, etc.), can be activated. When all docking conditions have been satisfied, a "ready for docking" indication can be displayed to the operator such as on the display monitor 58, control panel 50, etc.

Figure 2:
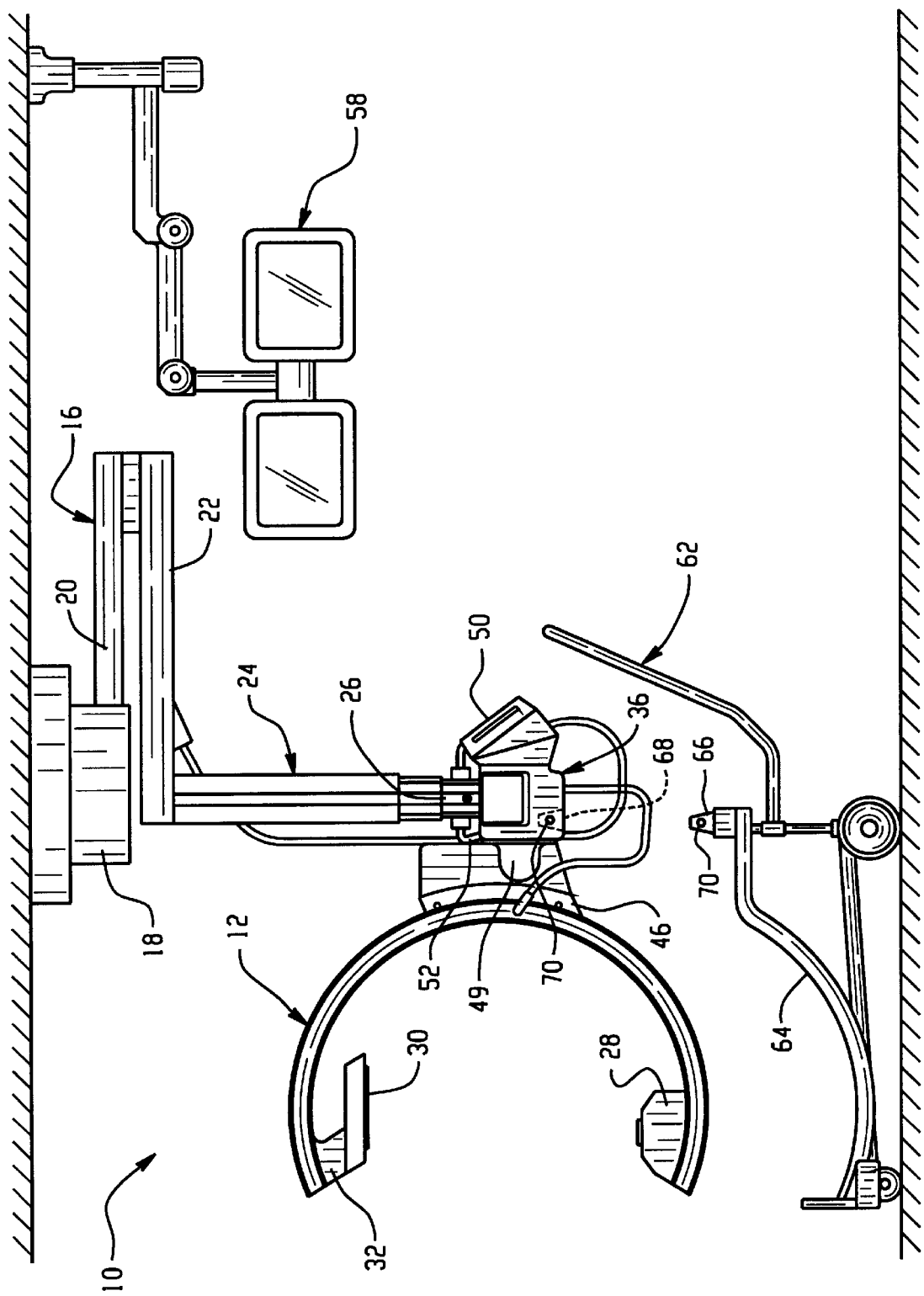
FIG. 2 illustrates a transport cart positioned below the C-arm of FIG. 1.

Thereafter, as shown in FIG. 2, a wheeled transport or docking cart 62 can be positioned beneath the suspended C-arm 12. The docking cart 62 includes a support surface 64 that substantially conforms to the contour of the C-arm 12 and coupler 36. An upright, substantially conical or tapered mount 66 projects from the support surface 64. The conical mount 66 is adapted to engage with a mutually conforming recess 68 associated with the coupler 36. Transverse bores 70 extend through the conical mount 66 and the recess 68, and are adapted to mutually align when the C-arm 12 is properly positioned on the cart 62.

Figure 3:
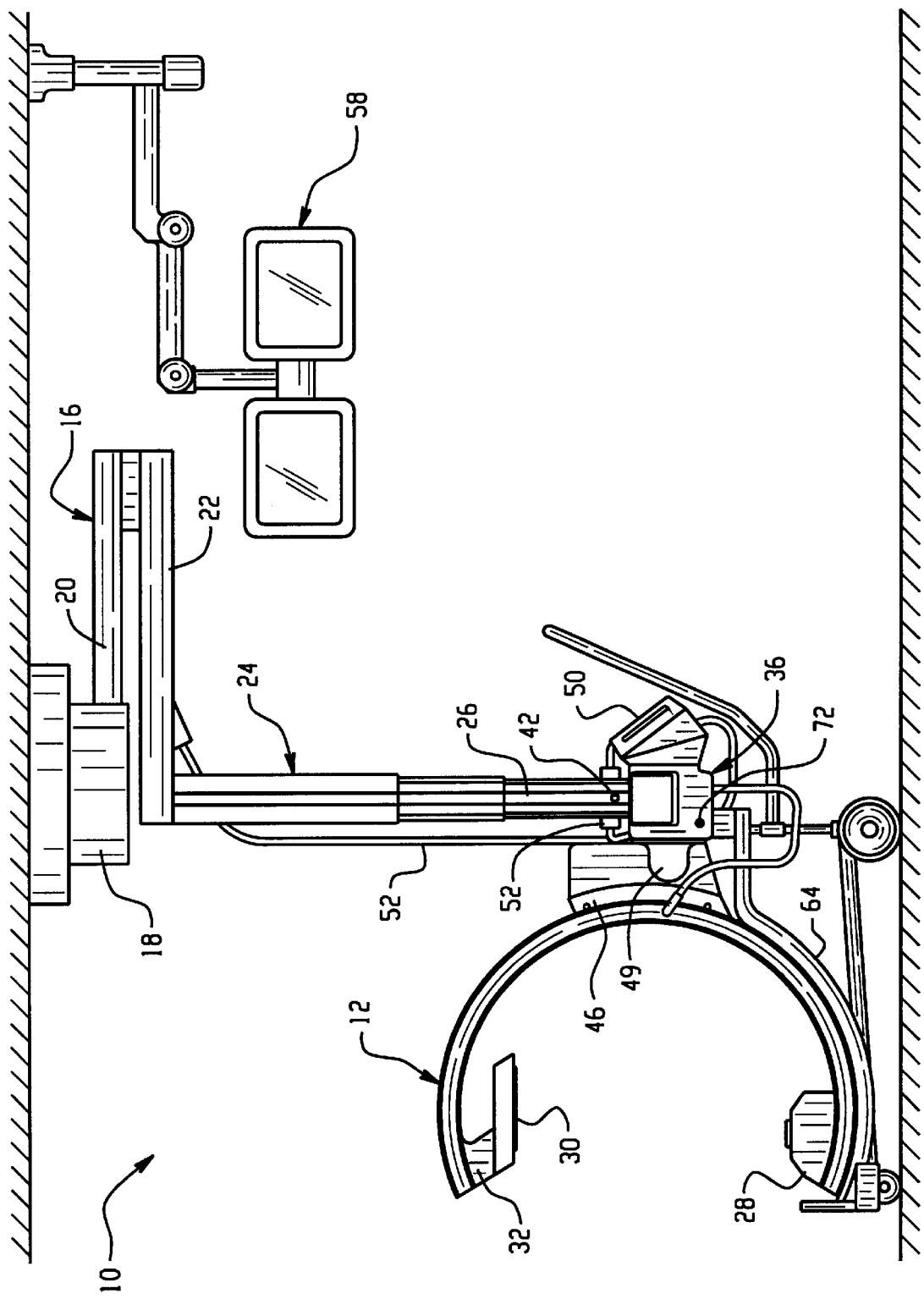
FIG. 3 illustrates the telescopic support arm in an extended configuration to lower the C-arm onto the transport cart of FIG. 2.

Referring now to FIG. 3, with the transport cart 62 generally positioned below the C-arm 12, a "docking" procedure can be initiated by activating a "docking" switch associated with the diagnostic imaging system 10 (e.g. upright column assembly 24, etc.). Initially, all pivot points associated with the mounting structure 16 are unlocked (i.e. energize/de-energize their associated solenoids) so that the C-arm can be accurately driven downward onto the cart 62 by the column assembly 24. A current limiting sensor stops the downward motion of the column assembly 24 when contact between the C-arm 12 and the cart 62 occurs. Thereafter, a locking pin 72 is inserted into the aligned bores 70, and the locking pin 44 is then removed from the bores 42. The locking pin 72 can be manually inserted into (and removed from) the aligned bores 70. Alternatively, the locking pin 72 can be solenoid-driven under command from the diagnostic imaging system 10. Further, the removal of the locking pin 44 can be automatically interlocked to the insertion of locking pin 72 to insure that the C-arm 12 is securely mounted to the cart 62 prior to release from the mounting structure 16.

Figure 5:
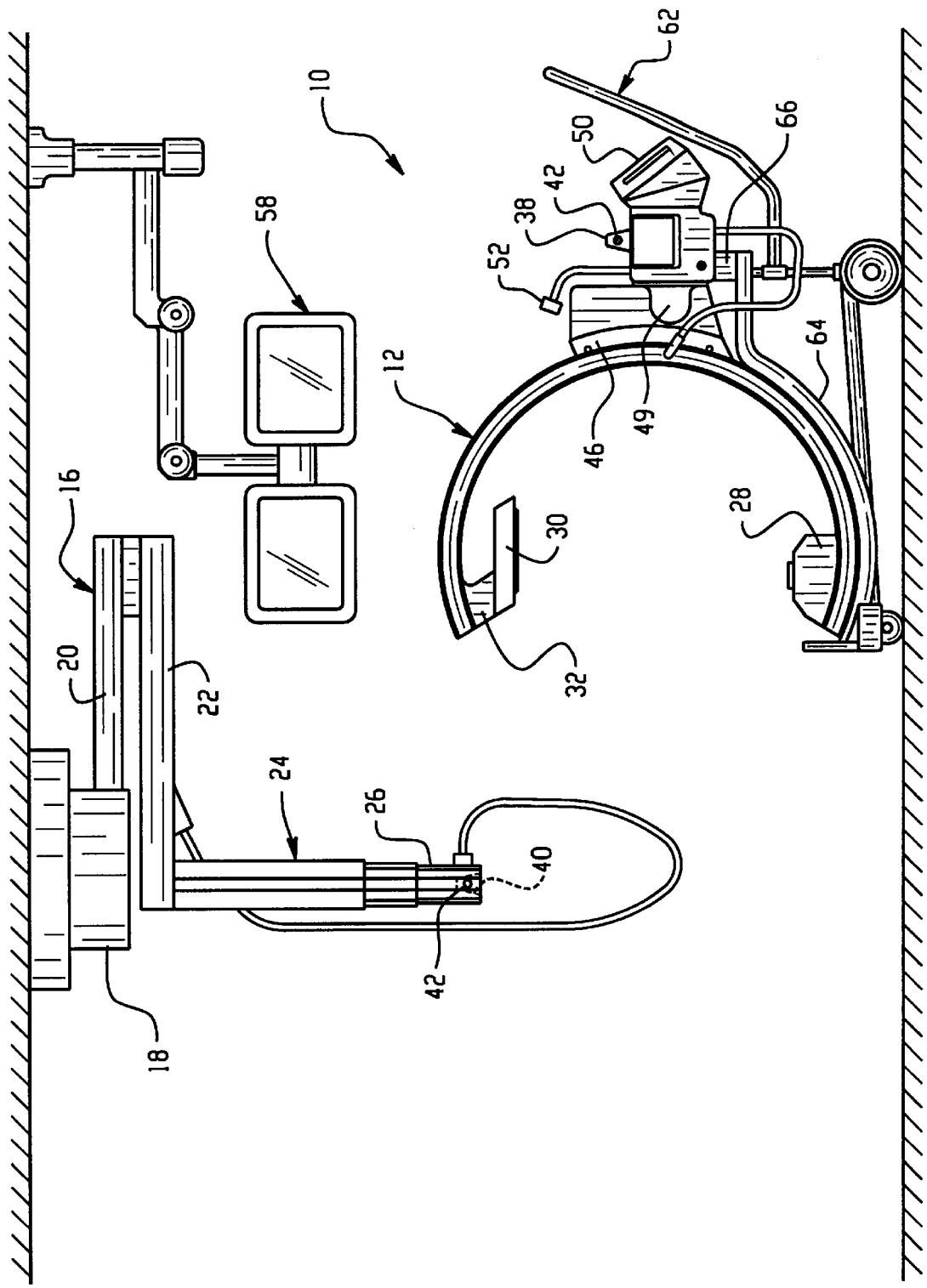
FIGS. 5 illustrates the transport cart and attached C-arm being moved away from the ceiling-mounted support arm.
Figure 6A:
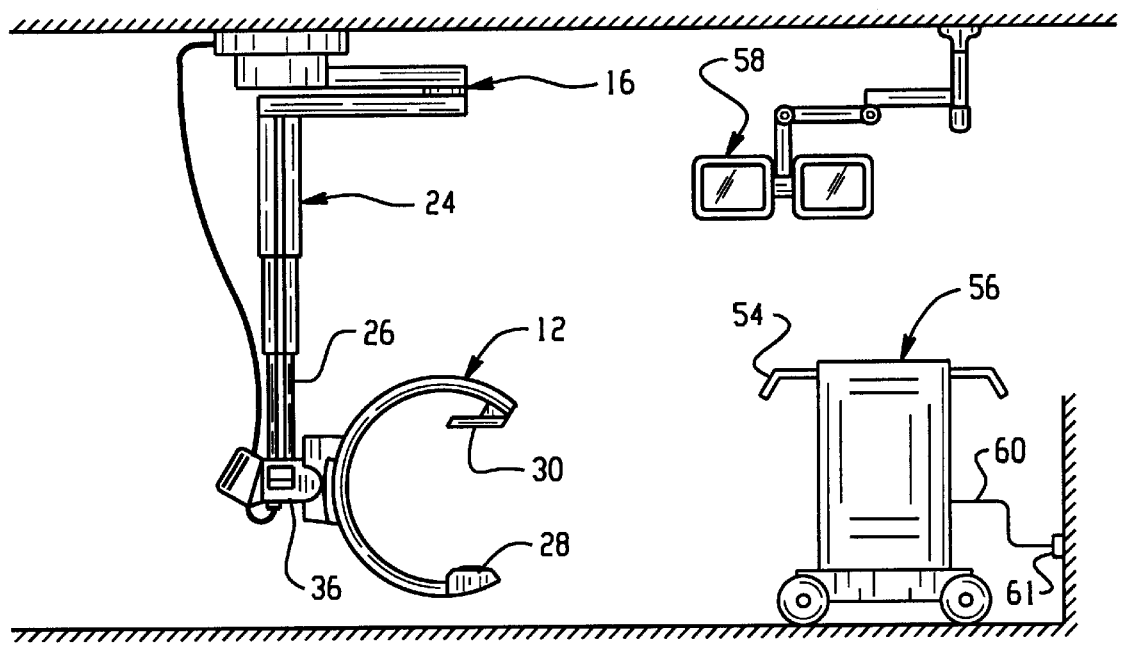
FIGS. 6a–6d illustrate the diagnostic imaging system of FIGS. 1–5 with a transportable electronics cart that accompanies the transportable C-arm.
Figure 6B:
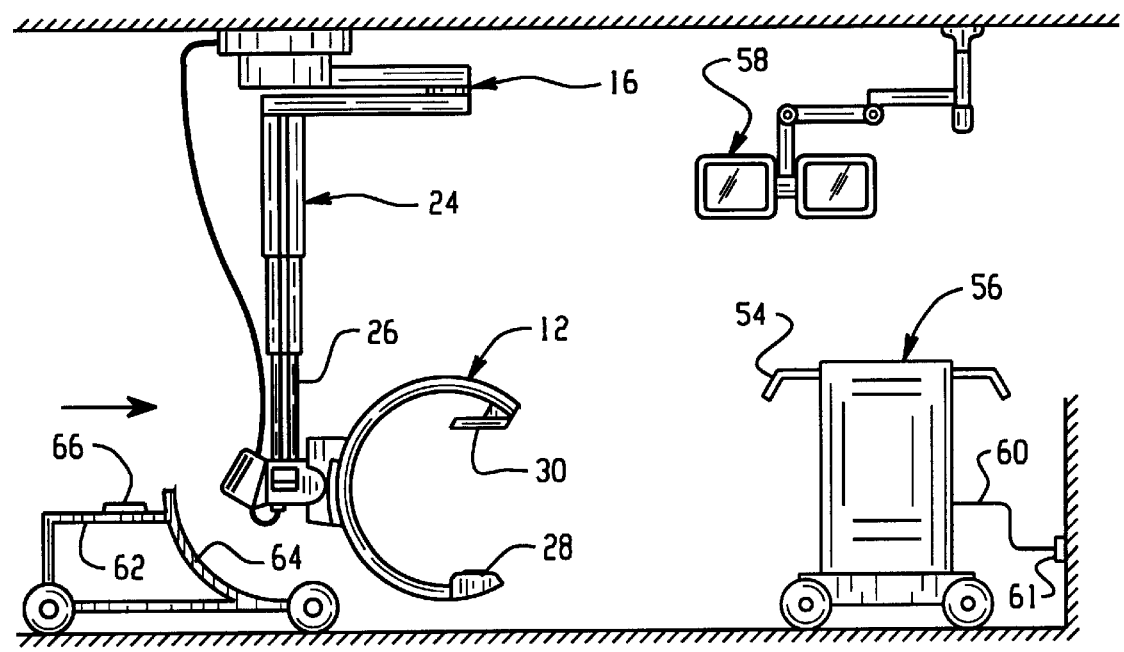
Figure 6C:
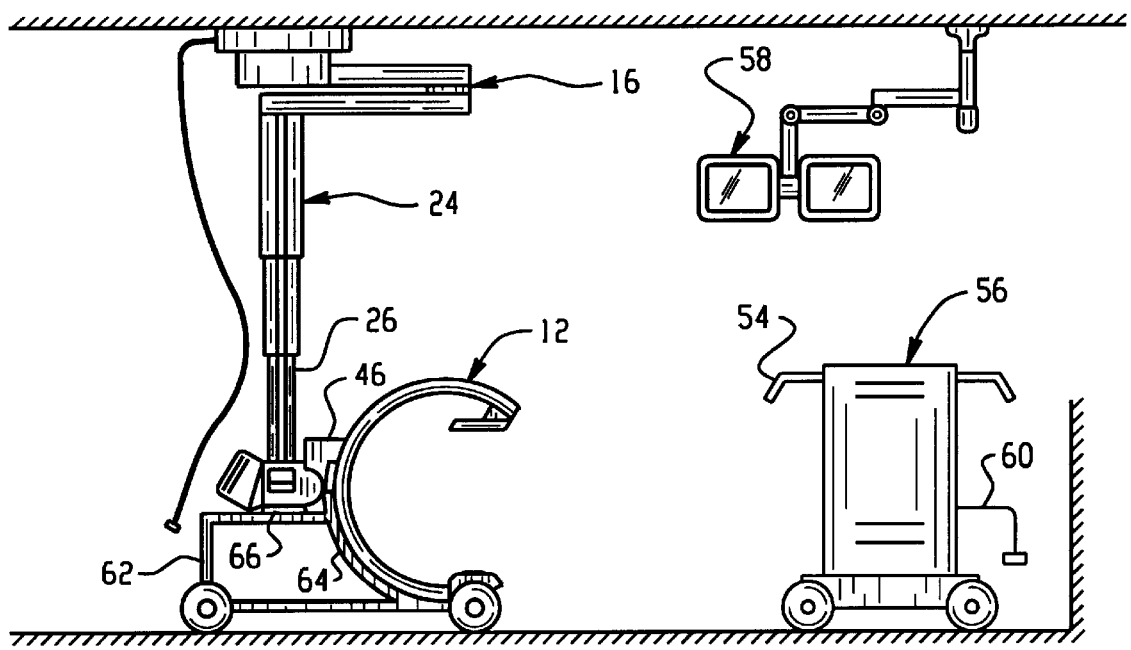
Figure 6D:
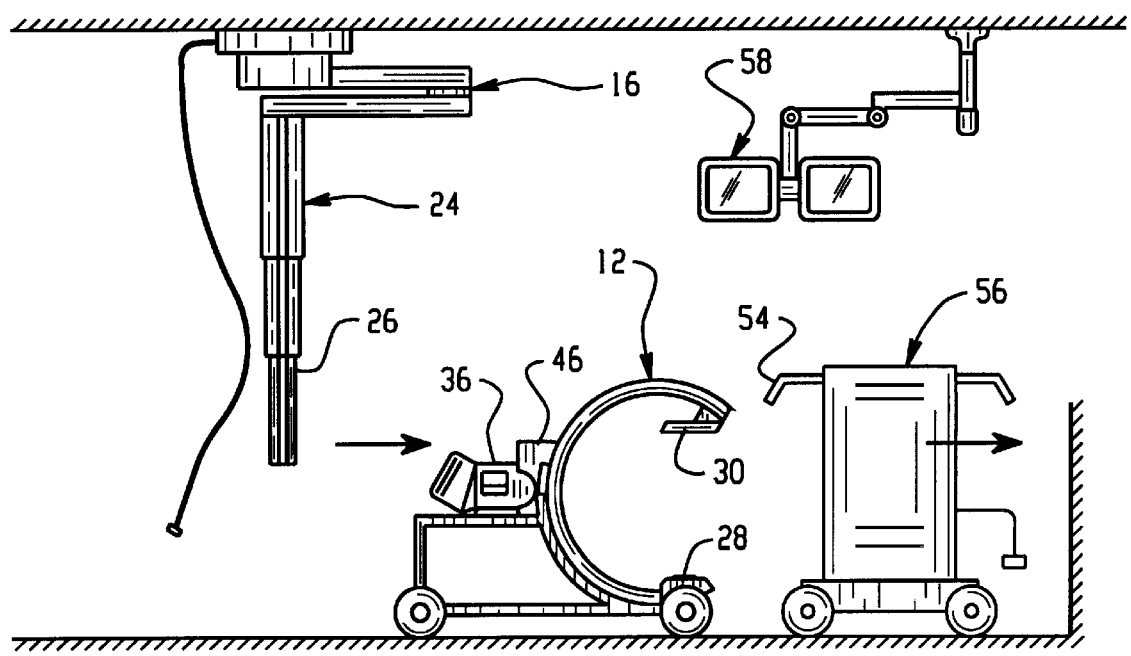
Figure 7A:
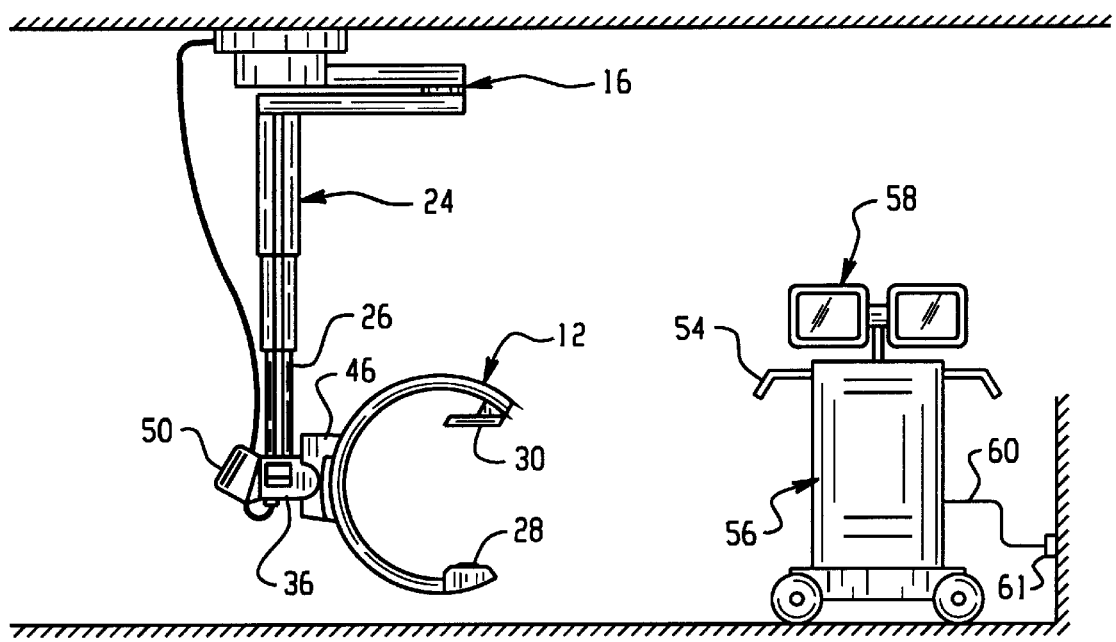
FIGS. 7a–7d illustrate another embodiment of a diagnostic imaging system with a transportable electronics cart having display monitors mounted thereto.
Figure 7B:
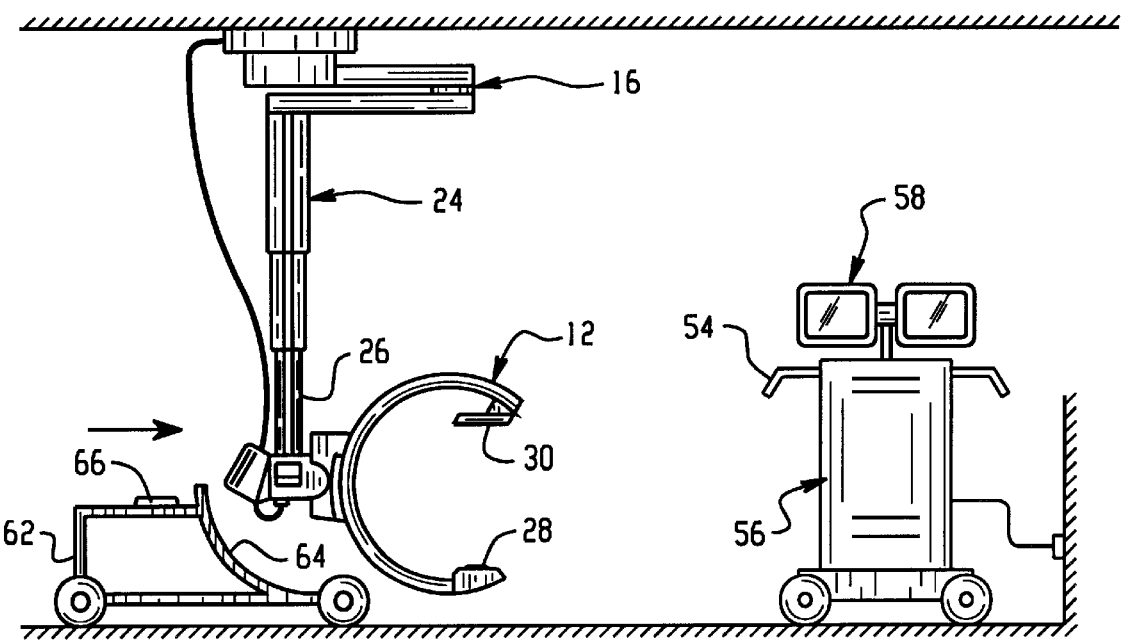
Figure 7C:
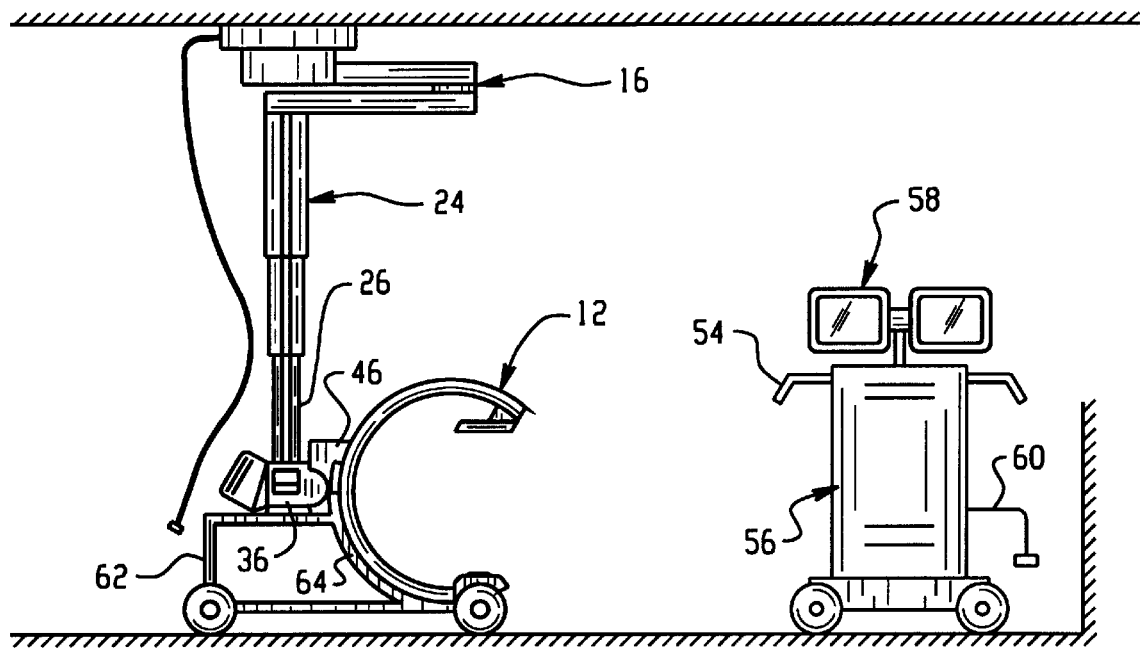
Figure 7D:
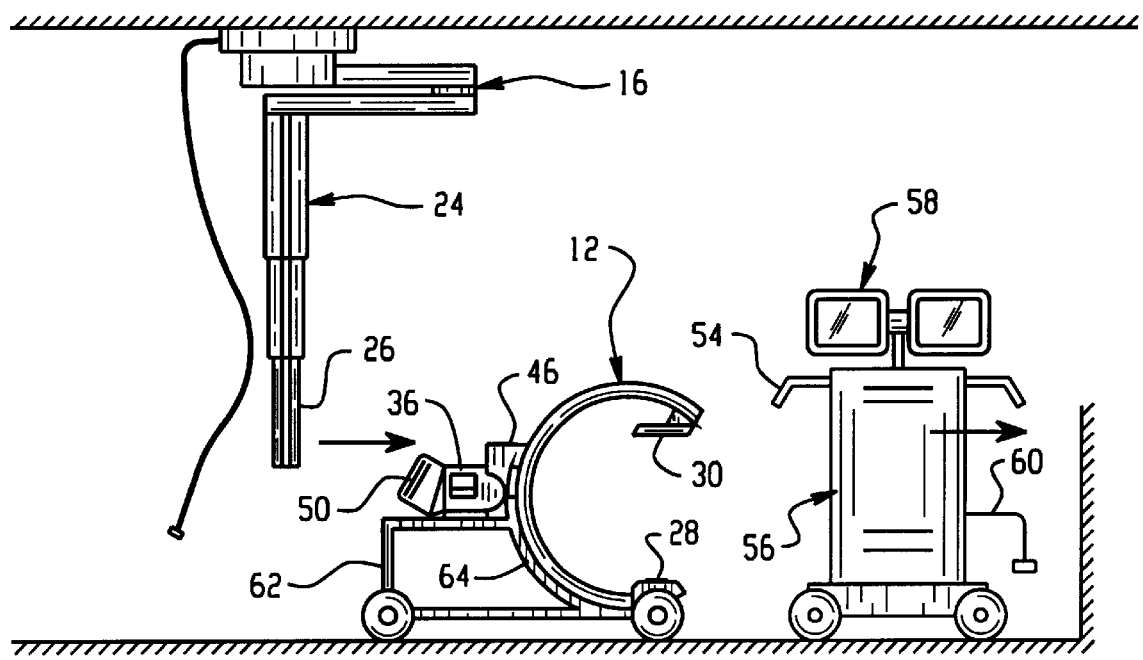

When the cables 52 between the mounting structure 16 and the coupler 36 are disconnected, the column assembly 24 can be driven upward out of contact with the C-arm as shown in FIG. 4. Lastly, the interlocks associated with the mounting structure pivot points can be engaged/disengaged to "park" the mounting structure 16. Thereafter, as shown in FIG. 5, the transport cart 62 and attached C-arm 12 can be safely transported to a different operating room where the C-arm can then be connected to a different mounting structure by reversing the docking procedure described above. It should be appreciated that utilizing a single C-arm 12 to support multiple operating rooms provides significant cost savings by eliminating redundant diagnostic imaging system components.

Referring again to FIGS. 6a–6d, it is contemplated that further cost savings can be achieved by permitting the wheeled equipment cart 56 and its associated processing hardware to accompany the wheeled transport cart 62 and attached C-arm to a different operating room. It may be desirable under certain operating conditions to provide uninterrupted power to the x-ray source 28 and/or x-ray detector 30 during transport. Accordingly, the equipment cart 56 can include a source of battery power that supplies power to various components (e.g. x-ray source 28, x-ray detector 30, etc.) of the imaging system 10 during transport.

With reference now to the embodiment of FIGS. 7a–7d, still further cost savings can be achieved by mounting the display monitor(s) 58 on the equipment cart 56 rather than configure each operating room with fixed, ceiling mounted, display monitor(s), as shown in the embodiment of FIGS. 1–6d.

Figure 8:
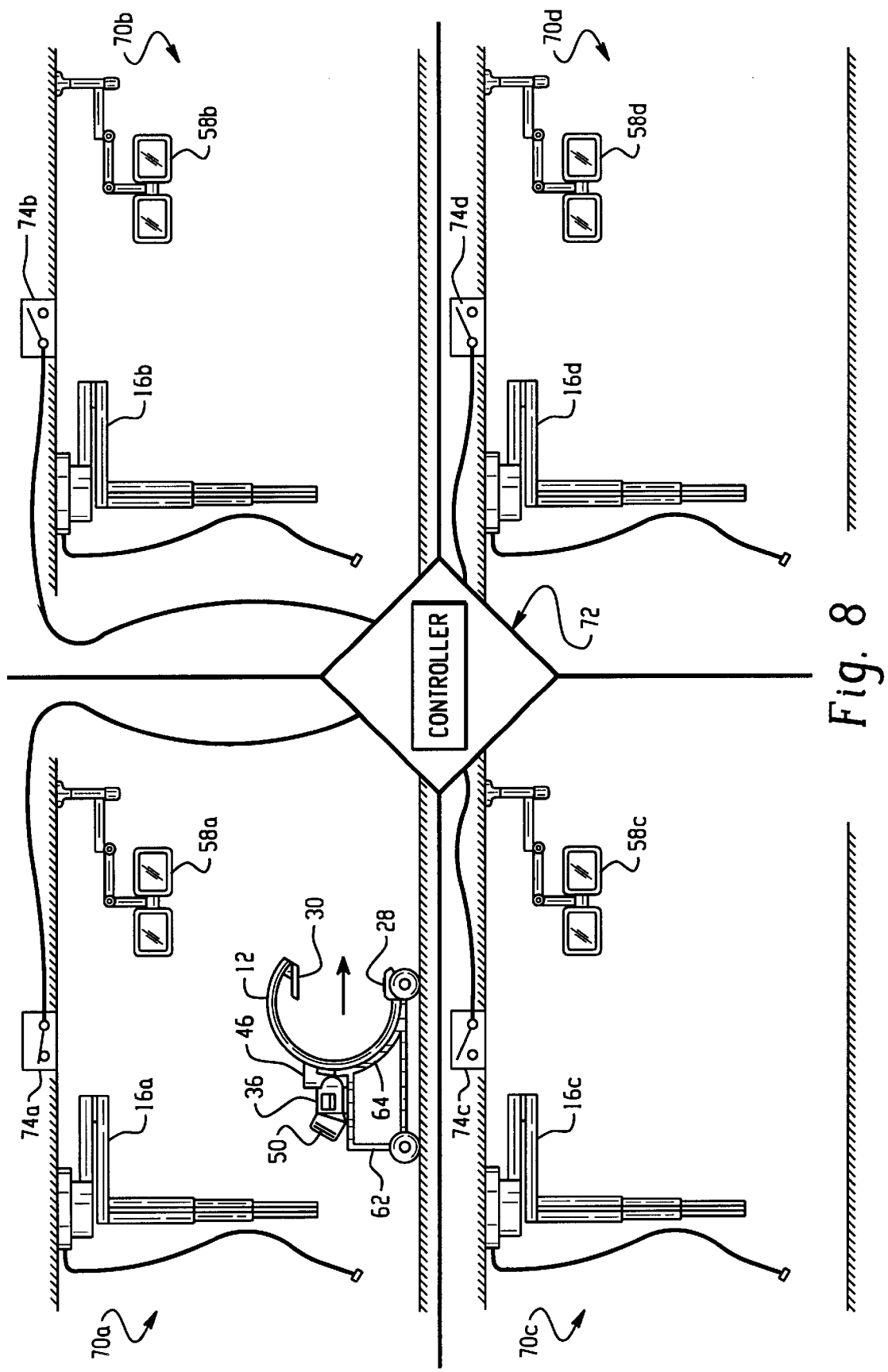
FIG. 8 is a plan view of a diagnostic imaging system with a central control facility that supports multiple surgical suites each having ceiling-mounted display monitors and a ceiling-mounted support arm adapted to receive a transportable C-arm in accordance with a further embodiment of the invention.
Figure 9A:
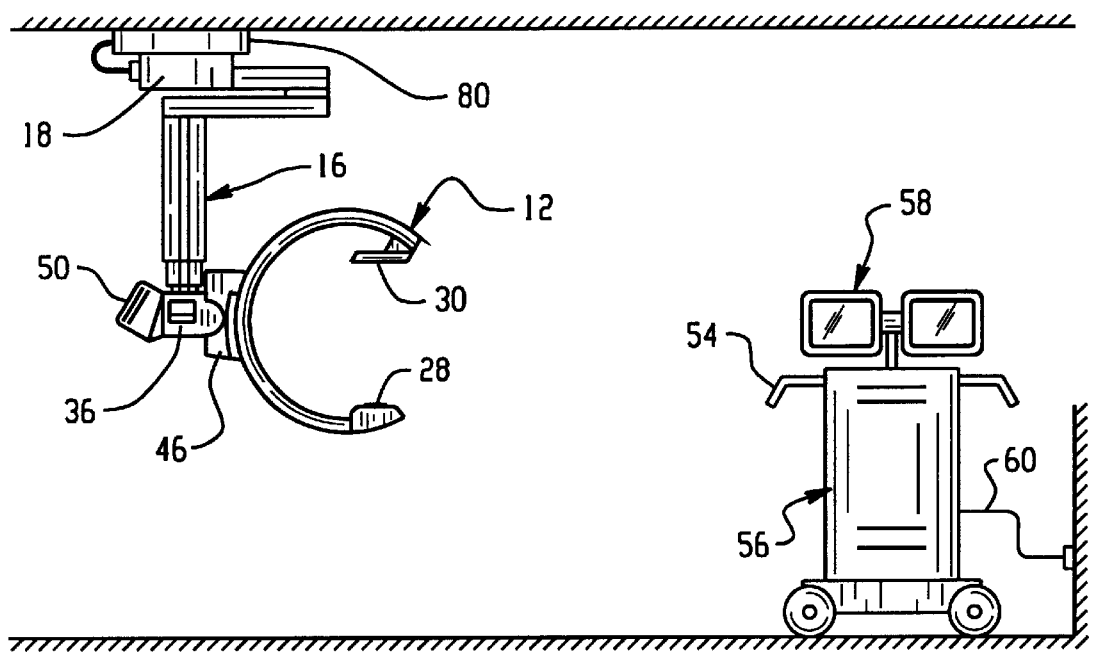
FIGS. 9a–9d illustrate yet another embodiment of a diagnostic imaging system with a transportable support arm and attached C-arm, and a transportable electronics cart with display monitors.
Figure 9B:
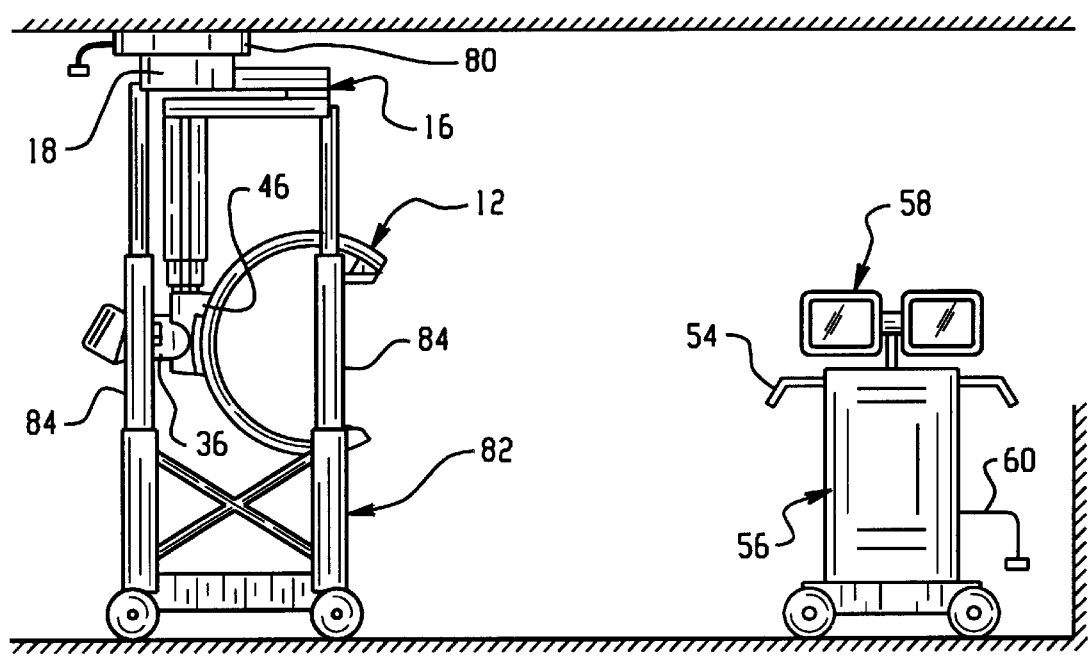
Figure 9C:
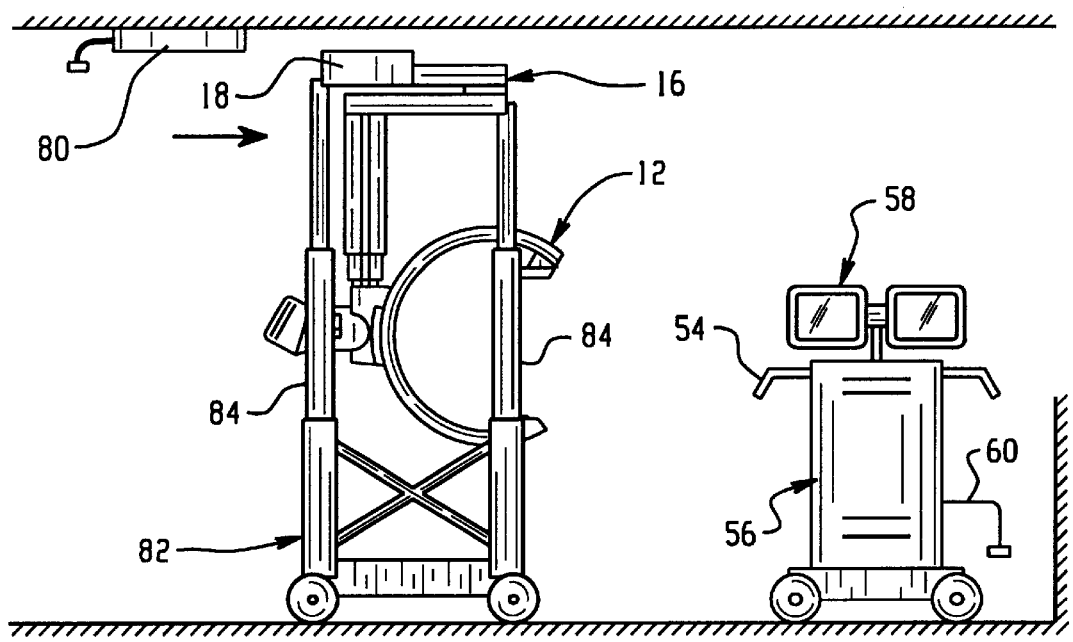
Figure 9D:
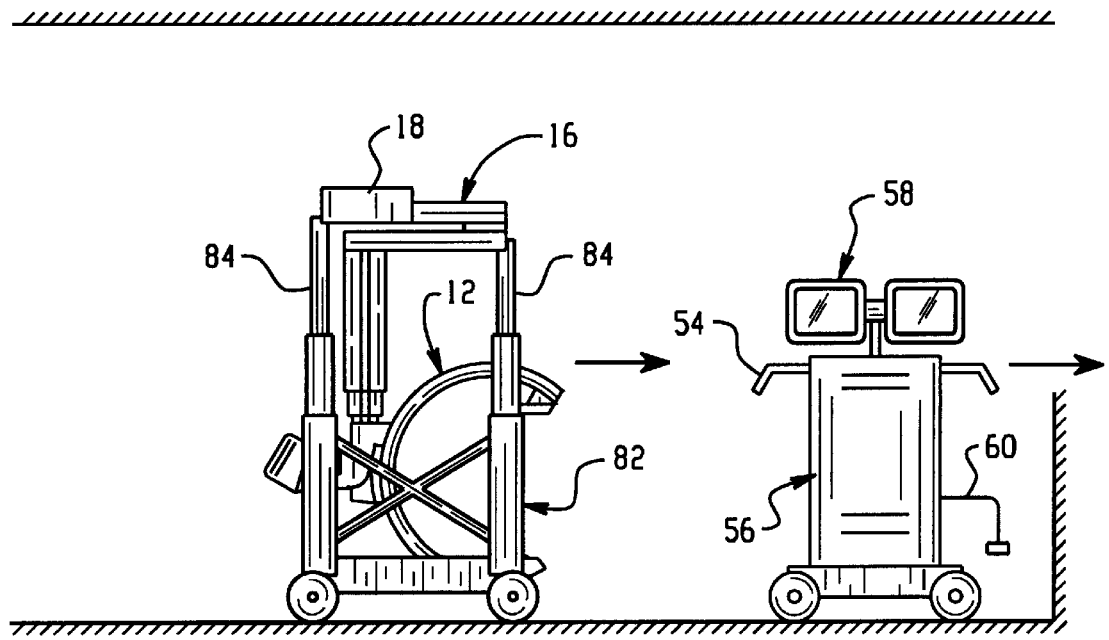

Referring now to the embodiment of FIG. 8, rather than provide a transportable equipment cart 56 that accompanies the transport cart 62 and attached C-arm 12, cost esavings can also be achieved by providing a surgical suite including a plurality of individual surgical rooms 70a–70d and a central control facility 72. Each of the surgical rooms 70a–70d includes a mounting structure 16a–16d suspended from its ceiling, along with ceiling-mounted display monitors 58a–58d. Further, at least one transportable C-arm 12 and transport cart 62 supports the surgical rooms 70a–70d. An interlock system including a plurality of switches 74a–74d connect the central control facility 72 to the C-arm 12 when attached to a particular mounting structure 16a–16d. As with the equipment cart 56 (FIGS. 6a–6d), the central control facility 72 includes known image reconstruction processing hardware and/or software for reconstructing an image representation from signals received from the x-ray detector 30. Preferably, the image reconstruction processor reconstructs a volumetric image representation from radiation attenuation data acquired by the x-ray detector 30 for display on the monitors 58a–58d.

Referring now to the embodiment of FIGS. 9a–9d, rather than provide a transportable C-arm 12 adapted to mount to a plurality of separate mounting structures 16, it is contemplated that the mounting structure 16 and attached C-arm 12 can be transported together as a single unit to different operating rooms. In particular, the base member 18 of the mounting structure 16 can be detachable from a fixed ceiling support 80. A wheeled transport cart 82 having adjustable (e.g. telescopic) support arms 84 can be raised and lowered to connect and disconnect the mounting structure 16 from the fixed ceiling support 80. Once disconnected from the ceiling support 80, the transport cart 82 and attached mounting structure 16 and C-arm 12 can be transported to a different operating room along with an accompanying equipment cart 56 and display monitors 58.

Figure 10:
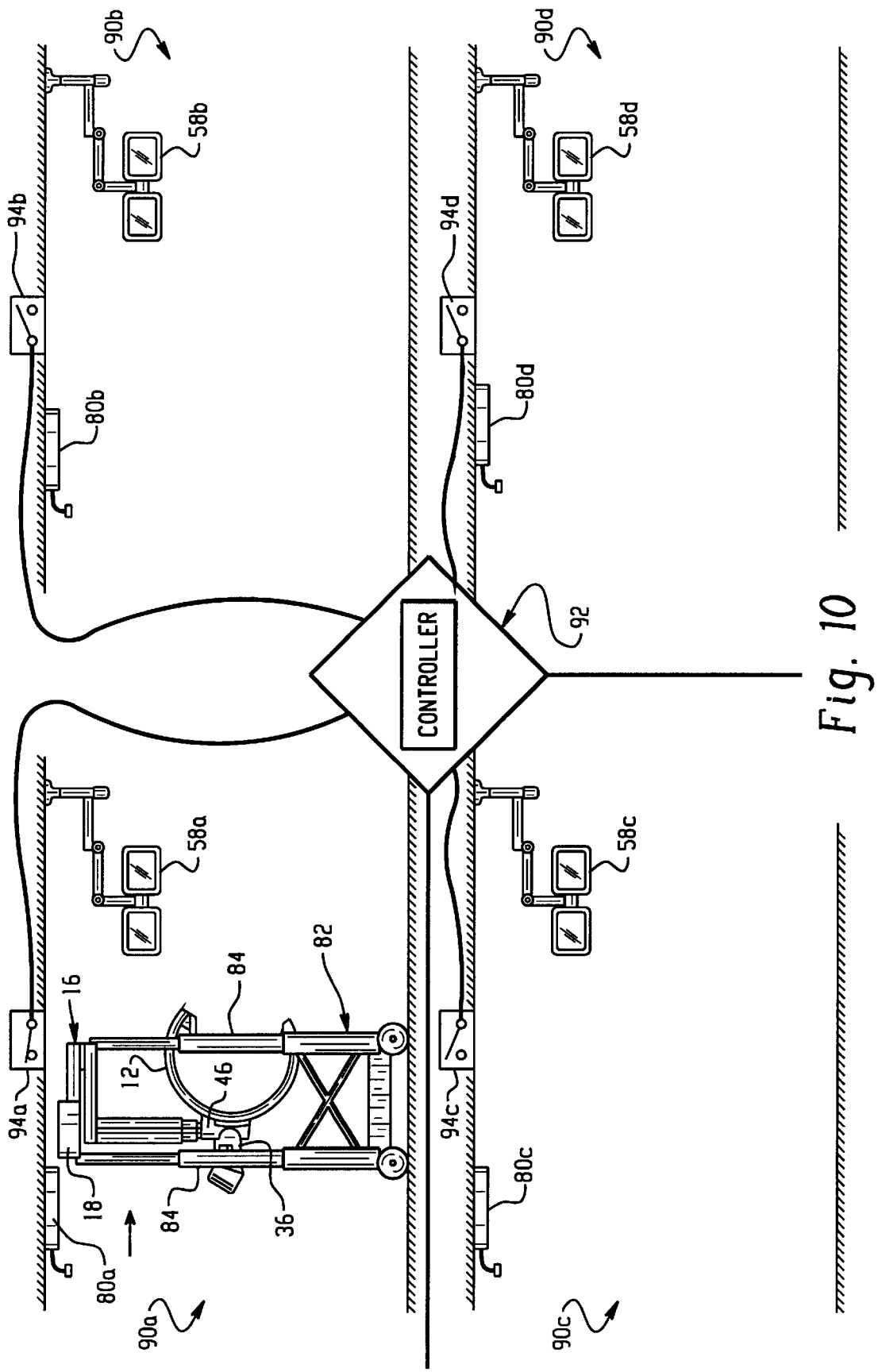
FIG. 10 is a plan view of a diagnostic imaging system with a central control facility that supports multiple surgical suites each having ceiling-mounted display monitors and a ceiling mount adapted to receive a transportable support arm and attached C-arm in accordance with yet another embodiment of the invention.
Figure 11A:
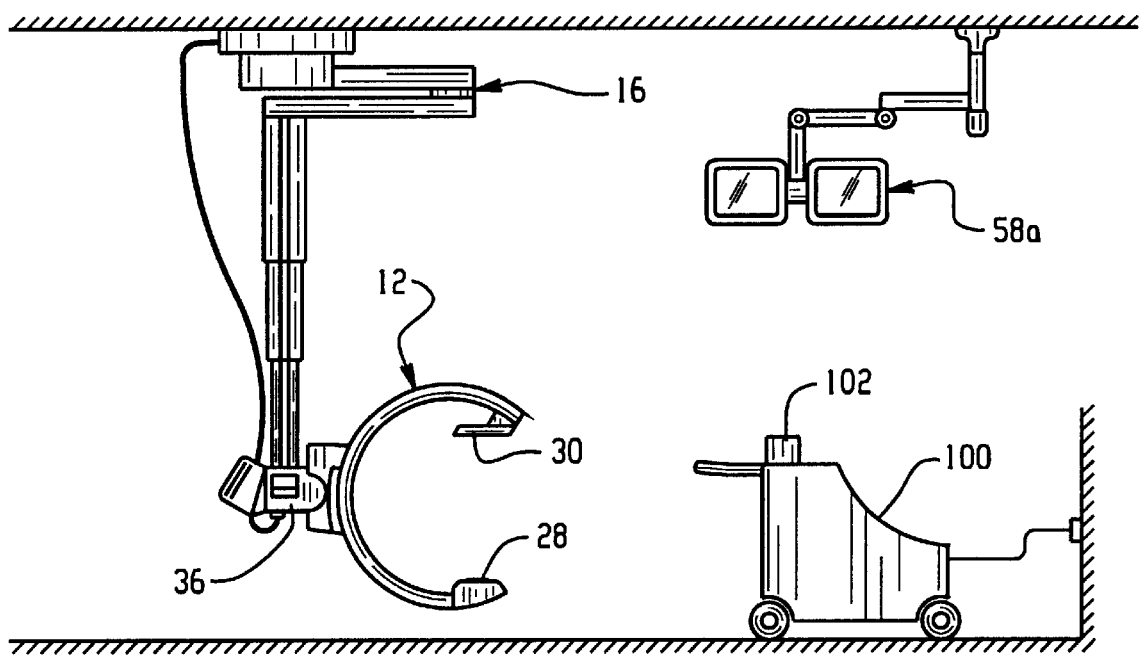
FIGS. 11a–11d illustrate a further embodiment of a diagnostic imaging system with ceiling-mounted display monitors and a transportable C-arm adapted to mount to a mobile cart.
Figure 11B:
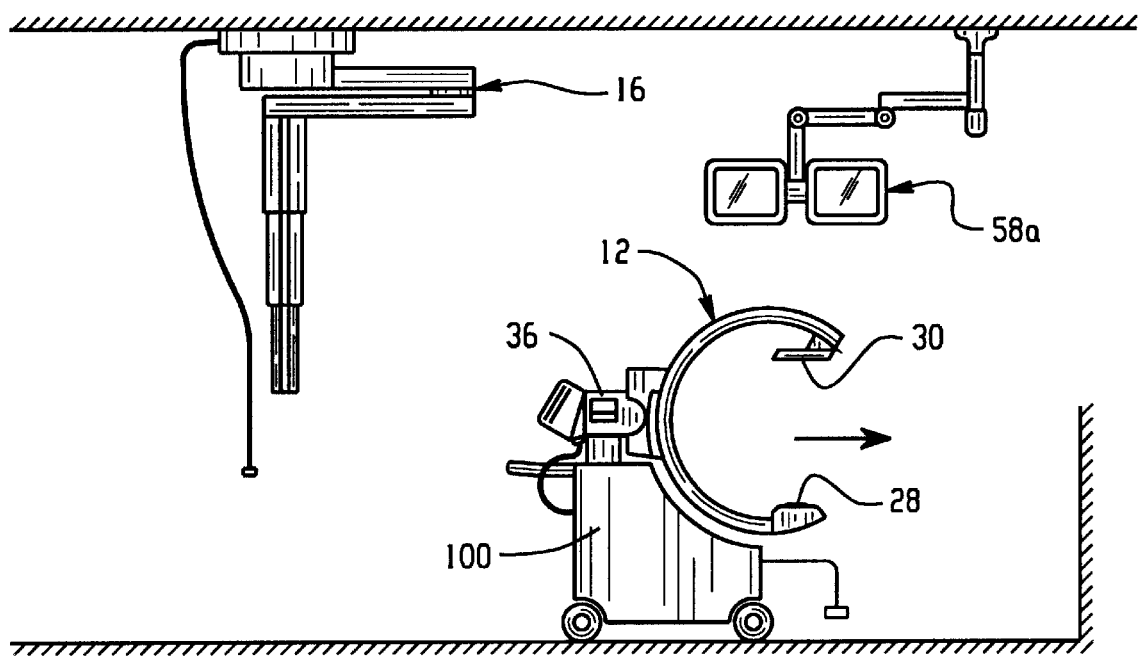
Figure 11C:
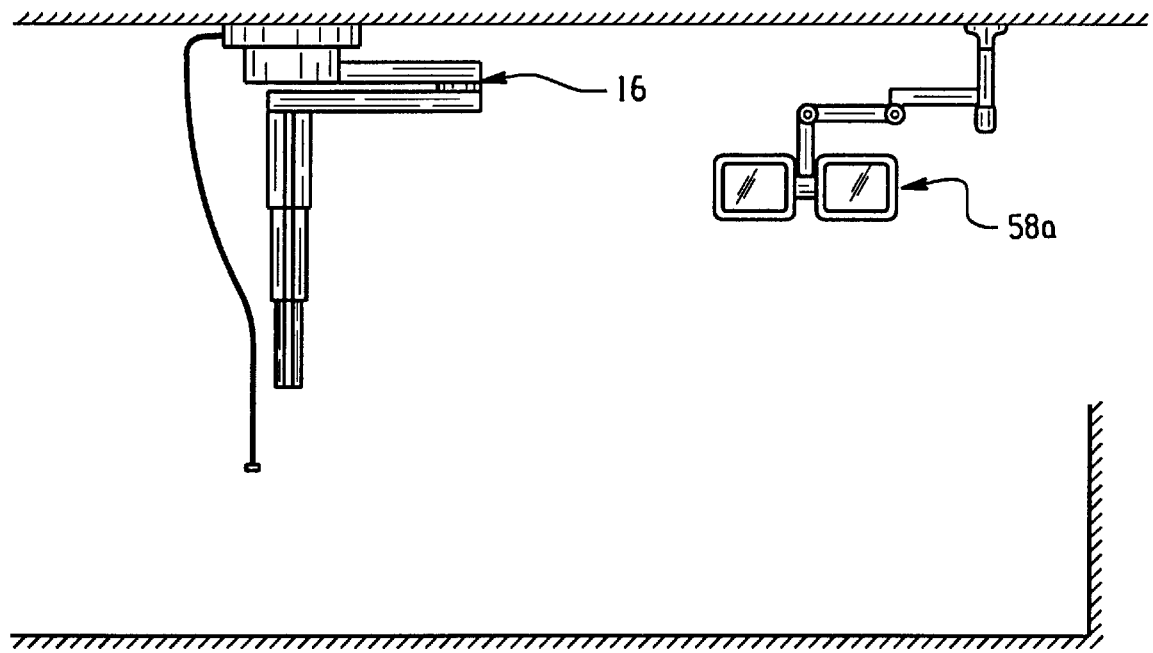
Figure 11D:
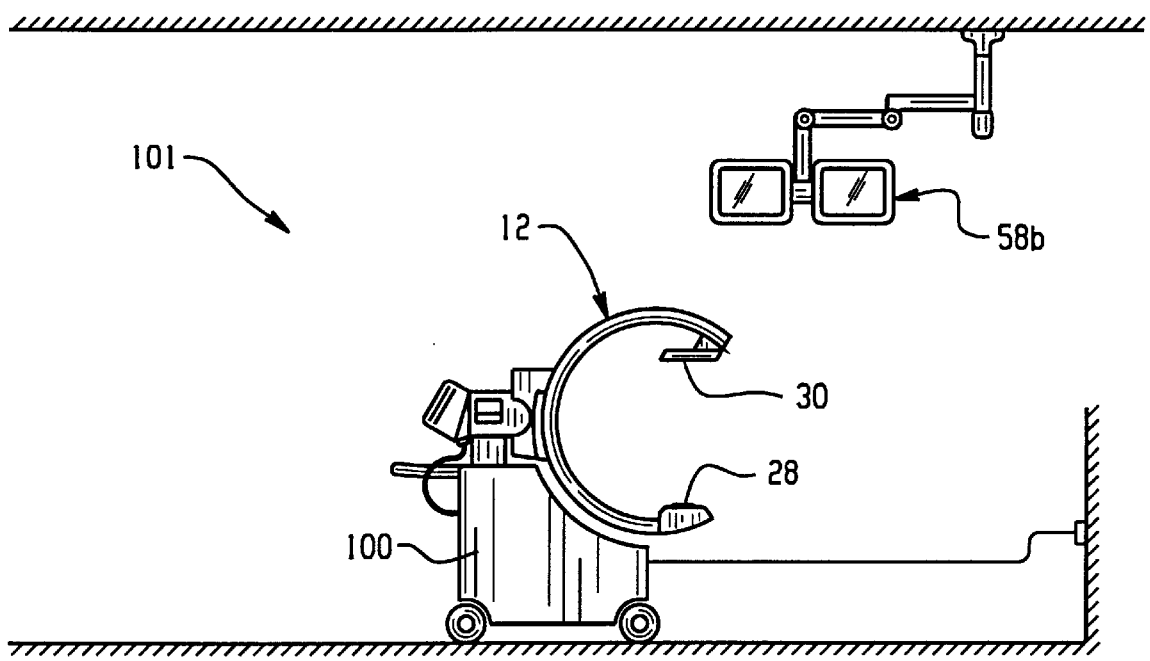
Figure 12A:
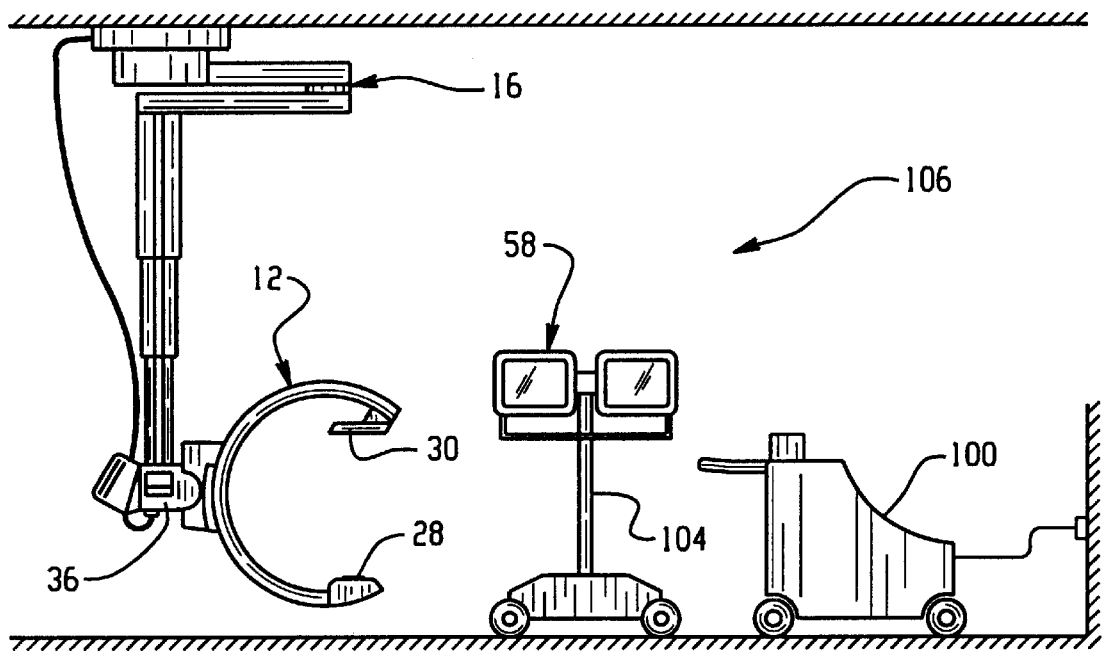
FIGS. 12a–12d illustrate a still further embodiment of a diagnostic imaging system with transportable display monitors and a transportable C-arm adapted to mount to a mobile cart.
Figure 12B:
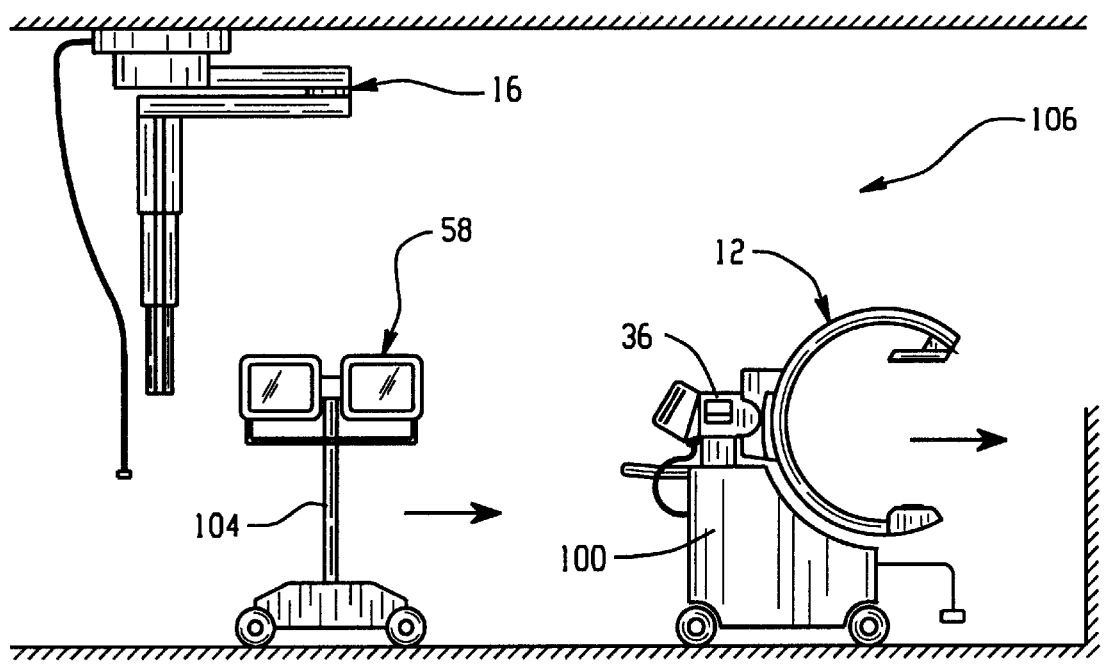
Figure 12C:
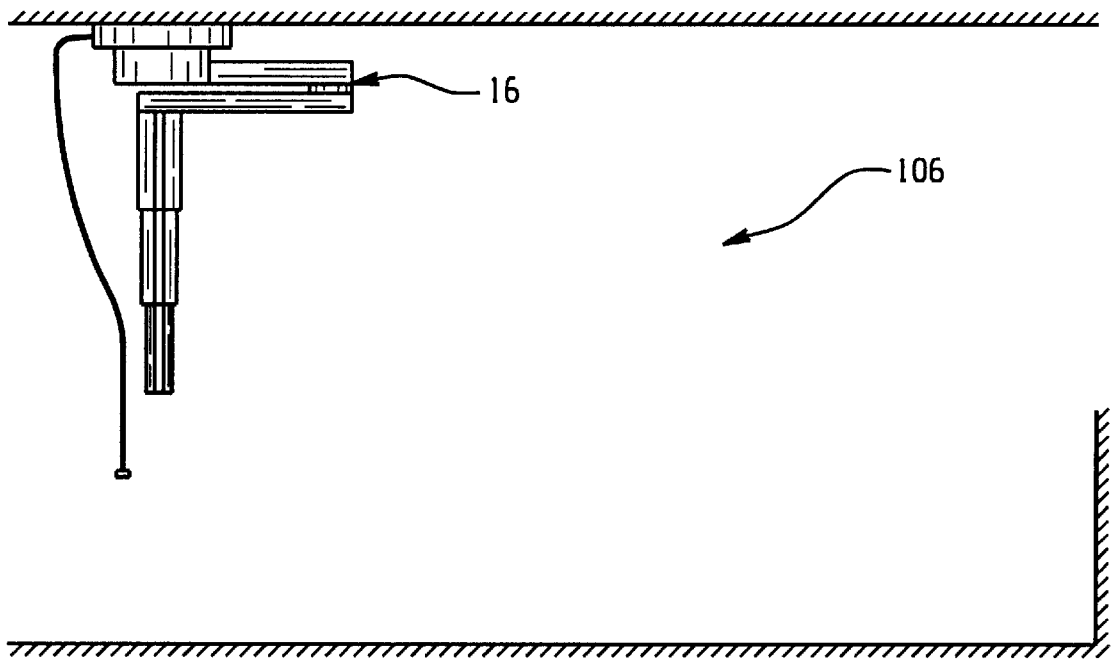
Figure 12D:
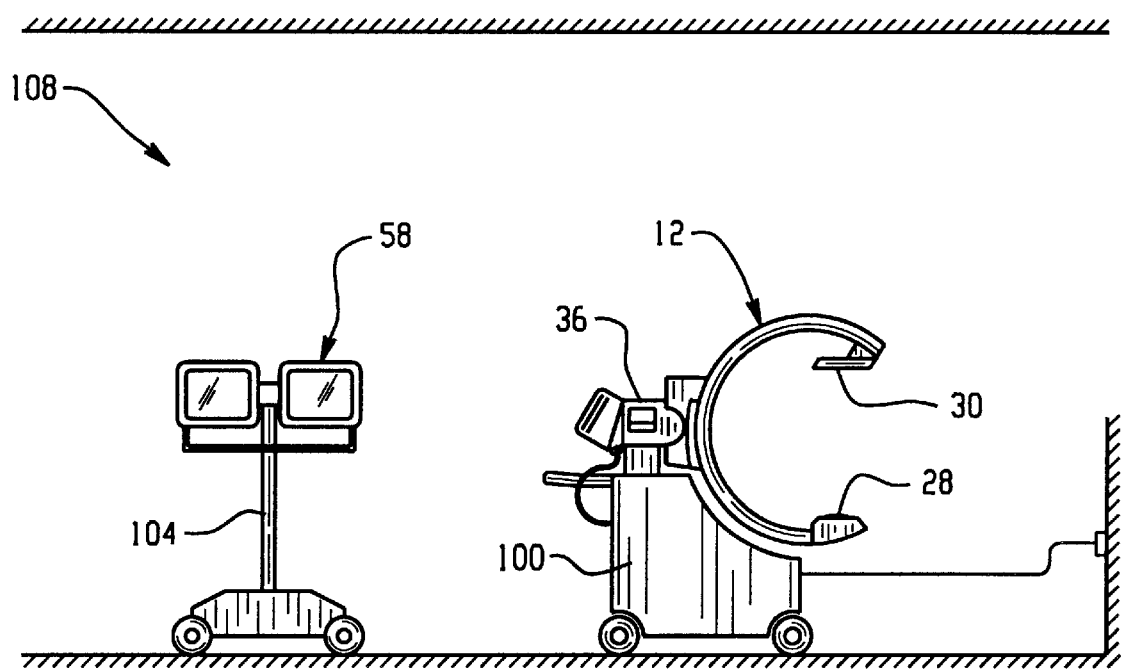

Referring now to FIG. 10, as with the embodiment of FIG. 8, cost savings can be achieved by providing a surgical suite including a plurality of individual surgical rooms 90a–90d and a central control facility 92. Each of the surgical rooms 90a–90d includes a fixed ceiling support 80a–80d suspended from the respective ceiling, along with ceiling-mounted display monitors 58a–58d. Further, at least one transportable mounting structure 16 and attached C-arm 12 and transport cart 82 supports the surgical rooms 90a–90d. An interlock system including a plurality of switches 94a–94d operatively connect the central control facility 92 to the C-arm 12 when attached to a particular fixed ceiling support 80a–80d. Like the central control facility 72 (FIG. 8), the central control facility 92 includes known image reconstruction processing hardware and/or software for reconstructing an image representation from signals received from the x-ray detector 30. Preferably, the image reconstruction processor reconstructs a volumetric image representation from radiation attenuation data acquired by the x-ray detector 30.

Referring now to the embodiment of FIGS. 11a–11d, it is contemplated that the C-arm 12 can be transferred between a fixed mounting structure (e.g. the ceiling-mounted mounting structure 16) and a mobile (e.g. wheeled) mounting structure 100, for use in a room 101 not configured with an overhead mounting structure 16. As with the cart 62, the mobile mounting structure 100 can include a mount 102 such as an upright, substantially conical or tapered mount that projects from a support surface of the mobile mounting structure 100. The mount 102 is adapted to engage with a mutually conforming recess associated with the coupler 36 of the C-arm 12. Transverse bores can extend through the mount and the recess, and mutually align with each other when the C-arm 12 is properly positioned on the mobile mounting structure 100.

In the embodiment of FIGS. 12a–12d, one or more display monitors 58 are mounted to a wheeled cart 104 that accompanies the mobile mounting structure 100 and attached C-arm 12 from a first room 106 to a second room 108 that is not configured with an overhead mounting structure 16, and is not configured with fixed (e.g. ceiling-mounted) display monitors.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

For instance, the mounting structure 16 can be configured as an overhead track system including ceiling mounted rails, a trolley that is movably secured to the rails, and a telescopic column assembly extending from the trolley. Further the support member 12 can be configured as a ring suspended from a mounting structure rather than as a C-arm, as disclosed in the above-mentioned U.S. Pat. No. 6,031,888.

What is claimed is:

1. A method of performing a diagnostic imaging procedure with a diagnostic imaging system including a mounting structure secured to a fixed surface at a first location, a support member removably secured to the mounting structure by a coupler, and an x-ray source and an x-ray detector secured to the support member, the method comprising:
   a) disconnecting the support member from the mounting structure;
   b) transporting the support member from the first location to a second location; and
   c) operating the x-ray source and the x-ray detector from a central control facility to perform a diagnostic imaging procedure at the second location.

2. The method of claim 1, further including:
   d) after the transporting step, attaching the support member to a second mounting structure secured to a second fixed surface at the second location.

3. The method of claim 1, wherein step b) includes the step of:
   d) transferring the support member to a mobile cart.

4. The method of claim 1, further including the step of:
   d) transporting an equipment cart along with the support member, the equipment cart including equipment that reconstructs an image representation from signals received from the x-ray detector.

5. The method of claim 1, wherein step c) includes the step of:
   d) operating a flat panel image receptor of the x-ray detector to convert x-ray energy to electrical signals.

6. A method of performing a diagnostic imaging procedure with a diagnostic imaging system including a mounting structure, a support member secured to the mounting structure, and an x-ray source and an x-ray detector secured to the support member, the method comprising:
   a) disconnecting the mounting structure from a first fixed surface;
   b) transporting the mounting structure and support member from a first location to a second location;
   c) attaching the mounting structure to a second fixed surface at the second location; and
   d) operating the x-ray source and the x-ray detector from a central control facility to perform a diagnostic imaging procedure at the second location.

7. The method of claim 6, wherein step d) includes the step of:

e) operating a flat panel image receptor of the x-ray detector to convert x-ray energy to electrical signals.

8. A diagnostic imaging system comprising:

a plurality of arm assemblies each mounted to a fixed surface in one of a plurality of diagnostic suites, each arm assembly having an arm coupler element and being configured to move the arm coupler element at least vertically within the room;

a support member which carries an x-ray source and an x-ray detector, the support member having a support member coupling element which is releasably connectable with the arm coupling element of each of the arm assemblies;

a cart for temporally supporting and moving the support member among the diagnostic suites for moving the support member among the mounting arms; and, a central control station from which the x-ray source and detector are controlled when the support structure is mounted to the arm assembly in any of the diagnostic suites.

9. The diagnostic imaging system of claim 8, wherein the support member includes a C-arm.

10. The diagnostic imaging system of claim 8 wherein the arm assembly is mounted to a ceiling of the associated diagnostic suite.

11. The diagnostic imaging system of claim 8 wherein one of the arm and support structure coupling elements is a male coupling element and the other of the arm and support structure coupling elements is a female coupling element and further including:

a pin which is inserted through aligned bores in the male and female coupling elements.

12. The diagnostic imaging system of claim 8 wherein the support member includes:

a C-arm which supports the x-ray source and the x-ray detector on opposite sides of an examination region;

a rotatable joint disposed between the support member coupling element and the C-arm which permits the C-arm to rotate the x-source and the x-ray detector around the examination region;

a drive for rotating the C-arm; and, a control panel mounted to the support member coupling elements for controlling at least the rotational drive.

13. The diagnostic imaging system of claim 12 further including:

a plurality of cables with first quick connects associated with the arm assembly and a plurality of electrical cables with quick connects for interconnecting with the arm cable quick connects associated with the support member.

14. A diagnostic imaging system comprising:

a plurality of diagnostic imaging suites;

a plurality of overhead arm assemblies, each of the overhead arm assemblies being mounted to a fixed surface of one of the diagnostic imaging suites, each of the overhead arm assemblies including a coupler at one end thereof;

a common C-arm assembly including:
a C-arm,
an x-ray source mounted at one side of the C-arm,
an x-ray detector mounted to an opposite side of the C-arm to define an examination region therebetween,
a rotatable mounting connected adjacent a mid-point of the C-arm to enable the x-ray source and x-ray detector to be rotated around the examination region, and,
a C-arm coupler which is selectively couplable with the coupler of each of the overhead arms for selectively coupling the C-arm assembly individually to each one of the overhead arms; and, a cart for transporting the C-arm assembly among the diagnostic imaging suites, whereby one C-arm assembly is shared among the plurality of diagnostic imaging suites.

15. The diagnostic imaging system of claim 14 wherein the cart includes:

a plurality of wheels;

a frame; and, a structure for mechanically supporting the C-arm assembly.

16. The diagnostic imaging system of claim 15, wherein the cart is configured to carry the C-arm assembly only and is free of electronic equipment.

17. The diagnostic imaging system of claim 14, further including:

a plurality of cables with first quick connects associated with the overhead arm assemblies and a plurality of electrical cables with quick connects for interconnecting with the overhead arm cable quick connects associated with the C-arm assembly.

18. The diagnostic imaging system of claim 14, further including:

a common control suite for controlling diagnostic imaging with the C-arm in each of the diagnostic imaging suites.

19. A method of performing diagnostic imaging procedures in which a plurality of overhead arm assemblies are each mounted in one of a plurality of diagnostic imaging suites, the method comprising:

(a) with a cart, moving a common C-arm assembly which carries an x-ray source and an x-ray detector among the plurality of diagnostic imaging suites;

(b) in one of the imaging suites, connecting the C-arm assembly with the overhead arm assembly;

(c) supporting the C-arm assembly with the overhead arm assembly and removing the cart;

(d) actuating the x-ray source and reading output data from the x-ray detector;

(e) reconstructing the data from the x-ray detector into a diagnostic image representation;

(f) lowering the C-arm assembly from the overhead arm assembly onto the cart;

(g) disconnecting the C-arm assembly from the overhead arm assembly;

(h) rolling the cart with the supported C-arm assembly to another imaging suite and repeating steps (b)–(e).

20. The method of claim 19 wherein the x-ray source and detector are controlled during diagnostic imaging procedures from a common control room.

* * * * *